United States Patent [19]

Smith et al.

[11] Patent Number: 5,073,344
[45] Date of Patent: Dec. 17, 1991

[54] DIAGNOSTIC SYSTEM EMPLOYING A UNITARY SUBSTRATE TO IMMOBILIZE MICROSPHERES

[75] Inventors: Michael W. Smith, Peachtree City; Robert S. Pierce, Smyrna, both of Ga.

[73] Assignee: Porex Technologies Corp., Fairburn, Ga.

[21] Appl. No.: 222,812

[22] Filed: Jul. 21, 1988

Related U.S. Application Data

[63] Continuation-in-part of Ser. No. 74,968, Jul. 17, 1987, abandoned.

[51] Int. Cl.⁵ .......................................... G01N 31/22
[52] U.S. Cl. ................................... 422/69; 210/632; 210/639; 210/500.27; 436/535; 436/541; 422/101
[58] Field of Search ............... 422/56, 60, 68.1, 69, 422/101; 436/535, 541; 210/510.1, 632, 639, 500.27, 500.36, 500.42; 264/86

[56] References Cited

U.S. PATENT DOCUMENTS

| | | | |
|---|---|---|---|
| 4,180,383 | 12/1979 | Johnson | 422/69 |
| 4,483,771 | 11/1984 | Koch | 210/490 |
| 4,613,567 | 9/1986 | Yasoshima et al. | 422/56 |
| 4,615,983 | 10/1986 | Koyama | 436/535 |
| 4,632,901 | 12/1986 | Valkirs et al. | 422/56 |
| 4,689,150 | 8/1987 | Abe et al. | 210/510.1 |
| 4,761,232 | 8/1988 | Bright | 210/500.36 |
| 4,774,192 | 9/1988 | Terminiello et al. | 436/530 |
| 4,837,145 | 6/1989 | Liotta | 436/541 |
| 4,894,157 | 1/1990 | Johnson | 210/500.3 |
| 4,916,056 | 4/1990 | Brown et al. | 422/57 |
| 4,933,092 | 6/1990 | Aunet et al. | 210/510.1 |
| 4,939,096 | 7/1990 | Tonelli | 436/541 |
| 4,952,516 | 8/1990 | Matkovich | 436/170 |

FOREIGN PATENT DOCUMENTS

| | | |
|---|---|---|
| 711286 | 7/1968 | Belgium . |
| 74161 | 12/1944 | Czechoslovakia ............... 422/60 |
| 207721 | 1/1987 | European Pat. Off. . |
| 2421035 | 11/1974 | Fed. Rep. of Germany ...... 436/541 |
| 2502508 | 10/1982 | France . |
| 55-132605 | 10/1980 | Japan . |
| 60-89757 | 5/1985 | Japan .............................. 436/535 |
| 8505451 | 12/1985 | World Int. Prop. O. . |

Primary Examiner—Richard V. Fisher
Assistant Examiner—John J. Bruckner
Attorney, Agent, or Firm—Lane, Aitken & McCann

[57] ABSTRACT

In a diagnostic apparatus system, a one piece porous substrate is located in a container. The substrate serves both to extract an antigen in or on a top layer with the remainder of the substrate serving as a reservoir. The pores in the top surface of the substrate are microscopic for entrapment of microspheres carrying antibodies. A target antigen in a test sample attaches to the antibodies when the test sample is poured through the top layer. The pores in all but the top layer of the substrate have a much greater pore size to define the reservoir portion of the substrate. The invention also includes a method of casting a microporous matrix in surfaces of a plurality of macroporous slugs. The method includes the steps of selecting a casting apparatus that defines openings for receiving the slugs and wells that are adjacent to the openings, positioning the slugs in the openings with the surfaces facing upward, the surfaces being positioned adjacent to the wells, dispensing a casting solution into the wells so that the solution contacts the surfaces, and allowing at least a portion of the solution to wick into the slugs and harden so that the microporous matrix is cast in the surfaces. The invention also includes an apparatus for practicing the method.

15 Claims, 3 Drawing Sheets

DIAGNOSTIC SYSTEM EMPLOYING A UNITARY SUBSTRATE TO IMMOBILIZE MICROSPHERES

The present application is a continuation-in-part of pending U.S. application Ser. No. 74,968, filed July 17, 1987 now abandoned.

The present invention relates to an improved diagnostic testing system of the type in which microspheres or other small particles are immobilized at or near the top surface thereof.

BACKGROUND OF THE INVENTION

A number of immunoassay systems have been developed utilizing immunologic technology. In these systems, the presence of an antigen in a test sample is detected by causing the antigen to bind to antibodies in a selected testing medium and then detecting the presence of the antigen in the testing medium. In a recently developed system, the testing procedure and the time to carry out the testing process has been substantially reduced so as to make it convenient to carry out the immunoassay process in a doctor's office or by a patient at home.

The prior art system, as shown in FIG. 1, comprises a container 11, housing an absorbent cylinder 13, which serves as a reservoir. On top of the reservoir is a porous plastic disk 15 on which is supported a porous membrane 17, usually separated from the porous plastic disk 15 by a porous contact pad 19. In the immunoassay process, antibodies specific to the antigen being detected are deposited on the membrane 17 by first bonding the antibodies or adsorbing the antibodies on microspheres of a synthetic resin such as polystyrene or latex and then depositing these microspheres in or on the membrane by passing liquid in which the microspheres are suspended through the membrane. A test sample to be tested for the presence of the suspect antigen is poured on the membrane 17 and is drawn through the membrane 17 relatively rapidly by capillary action of the reservoir 13 in combination with the porous plastic disk 15 and the contact pad 19. If the suspect antigen is in the test sample, it will bind to the antibodies deposited on or in the membrane. Following this step, liquid containing labeled antibodies specific to the suspect antigen is poured onto the membrane and is drawn through the membrane into the reservoir 13 by capillary action. If the antigen has been extracted from the test sample and retained in or on the membrane, the labeled antibodies will bind to the antigen and thus remain in or on the membrane 17. The application of the labeled antibody to the membrane will usually be followed by a rinsing step to remove unbound labeled antibody. This rinsing step is then followed by a step of causing the labeled antibody to exhibit its presence. In the case of an enzyme label, this last step is carried out by addition of a solution of a color-forming agent which reacts with the enzyme as the solution passes through it. As each liquid is passed through the membrane it is absorbed by the reservoir and the reservoir must be large enough to hold all of the volume of the test specimen, the labeled antibody solution, the rinse solution and the color-forming solution.

To obtain an accurate indication of the presence or absence of the antigen, the system must cause an even, consistent flow of the various liquids which are passed through the membrane. In order to achieve this even flow, contact between the various components of the system must be maintained. Any gaps between any two of the components will create pools of stagnant liquid and interfere with the capillary action drawing the liquid into the reservoir. This interference leads to erroneous or vague test results. Thus, when assembling the components of the system, great care must be taken to avoid trapping any particulate matter between the components, which particulate matter would create gaps between the components. The material of the membrane is available only as relatively large flat sheet and they must be cut into disks for use in the system. The assembly of the components is difficult because both the membrane and the contact pad are flimsy and manual assembly is usually required.

SUMMARY OF THE INVENTION

The system of the present invention is designed to overcome the above described problems in the prior art system. In accordance with the present invention, a one-piece porous substrate is provided in the container and serves both to extract the target substance in or on a top layer thereof with the remainder of the pore structure of the substrate serving as a reservoir. The pores in the top surface of the porous substrate are microscopic for entrapment of macroscopic particles such as microspheres. The pores in all but the thin top layer of the substrate have a much greater pore size and this portion of the substrate with the larger pores acts as a reservoir for the liquids to be passed through the top layer. Because the reservoir and layer in or on which the microspheres are entrapped are of one piece, the problems of assembly and the potential gaps between the components of the prior art system are avoided.

The invention also includes a method that produces a desired diagnostic system by casting a microporous matrix in surfaces of a plurality of macroporous slugs. The method includes the steps of selecting a casting apparatus that defines openings for receiving the slugs and wells that are adjacent to the openings, positioning the slugs in the openings with the surfaces facing upward, the surfaces being positioned adjacent to the wells, and dispensing a casting solution into the wells so that the solution contacts the surfaces. At least a portion of the solution is then allowed to wick into the slugs and harden, whereby the microporous matrix is cast in the surfaces.

DESCRIPTION OF A SPECIFIC EMBODIMENT

Figure 2:
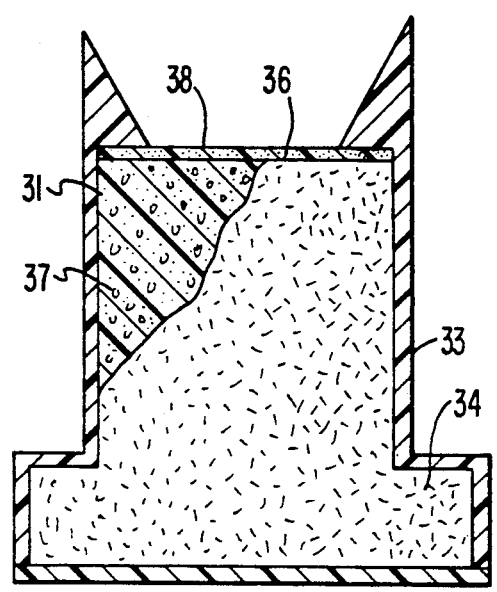
FIG. 2 is a sectional view illustrating the diagnostic apparatus of the present invention.

As shown in FIG. 2, the testing device of the present invention comprises a porous substrate 31 made of one piece contained within and filling a plastic container 33. The container may be made of two pieces to facilitate inserting the substrate into the container. The substrate 31 is cylindrical in shape and has an enlarged section 34 at the bottom. The pores of the substrate are interconnected into tortuous capillary passageways so that the substrate is absorbent. The substrate is provided with a top layer 36 having smooth flat top surface 38. The pores that provide the porosity to the top layer and surface are much smaller than in the lower portion 37 of the substrate which functions as a reservoir for the substrate and which comprises the major portion of the substrate.

The reservoir 37 may be described as macroporous, meaning that the pores of the reservoir are visible without the aid of a microscope. The pore size range in the reservoir 37 is from 20 to 100 microns and the pore volume is between 35% to 65%. Normally a pore volume of 50% or greater is preferred and is necessary in some immunoassay applications. The pores in the top surface are preferably of a size that the top surface can be described as being microporous, which means that the pores in the top surface are so small that they can only be seen with the aid of a microscope.

To condition the device as described to be used in a testing process, microscopic particles, such as microspheres, must be deposited on or in the top surface of layer 36. The particles may also be trapped down in the top layer, by passing part way through the top layer before becoming entrapped. However, for the clearest indications of test results, it is preferred that the particles be trapped at the top surface. The particles may range in size from 0.1 microns to several microns in diameter. Particles larger than 5 microns may be employed, but smaller particles in the range of 0.1 microns to 5 microns are preferred, because smaller particles provide a greater concentration of surface area for the binding of a target substance to take place. Extremely small particles are not used because they would require correspondingly fine pores in the top surface of the substrate and the smaller the pore size in the top surface, the longer it takes the liquids in the immunoassay process to pass through the top layer into the reservoir. As a compromise between the competing concerns of obtaining a high concentration surface area and a rapid passing of the liquids through the top surface into the reservoir, microspheres of about 1 micron in size are most often selected. However, in some applications, such as when the sample to be tested contains low concentrations of a target antigen, a slower flow rate is desirable in order to give the antigen in the sample a longer time to react with the antibodies on the microspheres.

Figure 1:
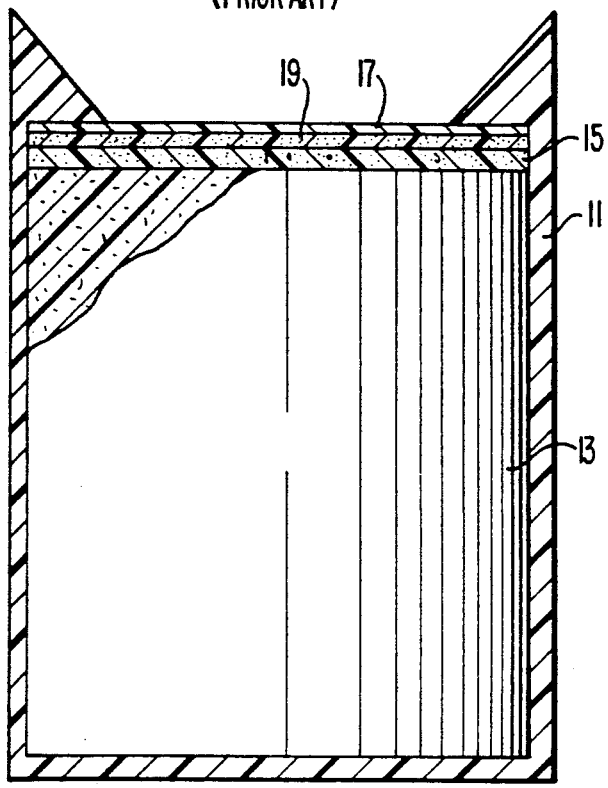
FIG. 1 is a sectional view illustrating immunoassay apparatus of the prior art.

To deposit microspheres on the top surface of the substrate, the microspheres are suspended in an aqueous solution or a liquid which will wick readily into the substrate. A drop of the suspension containing the microspheres is placed on the top surface of the substrate and the liquid of the suspension wicks down into the substrate, leaving the microspheres captured on or embedded in the surface of the substrate. The pore size of the top layer should be small enough so as to capture the microspheres on the top surface either by filtering action alone or in combination with a tendency of the microspheres to agglutinate and adhere to the material of the substrate. Usually, it is preferred that the pore size in the top surface should be as large as possible while still being effective to entrap the microspheres on or in the surface, unless a longer incubation time is needed in which case the pore size will be selected to provide the desired incubation time. In any event, the pore size of the top surface should be much smaller than the pore size of the reservoir which, as in the prior art system described with reference to FIG. 1, will function to draw liquids through the top layer by capillary action during the immunoassay test process. After the liquid of the suspension has wicked down into the substrate, with the microspheres being captured on the top surface 34 of the substrate, the liquid of the suspension is allowed to evaporate, leaving the dried microspheres captured at or on the surface of the substrate. Preferably, the microspheres are immobilized on the substrate surface. This preferred immobilization is aided by agglutination of the microspheres and/or adherence of the microspheres to the material of the substrate.

The apparatus in this form, with the microspheres deposited on the surface of the substrate, is provided to the user who will carry out a testing process to test for the presence of a target substance. This testing process may be carried out substantially in the same manner as described above with respect to FIG. 1 and also as described in U.S. Pat. No. 4,632,901 to Valkiers et al., issued Dec. 30, 1986, which is hereby incorporated by reference. Specifically, the microspheres deposited on the top surface of the substrate have bound or deposited on their surfaces antibodies, which are selected to be specific to the target antigen. A test sample to be tested for the presence of suspect antigen is poured on the top layer 36. The test sample is drawn through the top layer 36 relatively rapidly by the capillary action of the reservoir 37. If the suspect antigen is in the test sample, it will bind to the antibodies on the microspheres deposited on the top surface of the substrate. Following the application of the test sample to the substrate, a liquid containing labeled antibodies specific to the suspect antigen is poured onto the top layer and is drawn through the top layer into the reservoir 37 by capillary action. If the antigen has been extracted from the test sample and retained at the top surface of the substrate, the labeled antibodies will bind to the antigen and thus remain at the top surface. As in the prior art process, the application of the labeled antibody to the top layer will usually be followed by a rinsing step to remove unbound labeled antibody from the top layer. This rinsing step is then followed by a step of causing the labeled antibody to exhibit its presence. In the case of an enzyme label, this last step is carried out by the addition of a further solution of a color-forming agent which reacts with the enzyme as the solution passes through the top layer 36.

As each liquid is passed through the top layer, it is absorbed into the reservoir 37. Accordingly, the reservoir must be large enough to hold all of the volume of the test specimen, the labeled antibody solution, the rinse and the color-forming solution. The apparatus of the invention may also be used in an immunoassay process, which tests for the presence of target antibodies in a test sample. In such a process, an antigen specific to the target antibodies is bound to or adsorbed on the surfaces of the microspheres or other small particles, and the target antibodies will bind to the antigen as the test sample is wicked through the top surface of the substrate. The apparatus of the invention may also be used in other diagnostic testing processes for detecting the presence of target substances in test samples other than immunoassay processes. To test for the presence of a target substance, a material which will adhere to the target substance is bound to or adsorbed on the surface of the small particles, or, alternatively, the material of the small particles themselves is selected so that the target substance will adhere to the material of the small particles. Then when the test sample is wicked through the top surface of the top layer of the substrate, the target material will be extracted in or on the top surface of the substrate, where its presence is detected.

The one piece porous substrate with the top surface 38 having fine pores to trap the small particles on the surface is manufactured in different embodiments by more than one process. In accordance with one embodiment, the porous substrate comprises sintered particles of synthetic resin with a top layer 36 being made from sintered particles smaller than the particles which are sintered together to form the reservoir. To facilitate forming the porous substrate by the methods described herein, the synthetic resin is thermoplastic, but any synthetic resin that can be formed into an open-celled macroporous substrate is suitable. The material of the resin is naturally hydrophilic or capable of being rendered hydrophilic such as by means of a surfactant. The material is biochemically inert or is capable of being rendered biochemically inert as by the application of a blocking agent to an otherwise non-inert surface.

A preferred synthetic resin for the substrate is an ultra high molecular weight polyethylene, such as GUR 400 Series, GUR 413, and GUR 212, all manufactured by Hoechst Celanese Corp. of Houston, Tex., and HB301s/-HB312, manufactured by Himont Corp., Wilmington, Del. In a preferred embodiment, GUR 400 Series ultra high molecular weight polyethylene is screened minus 150 mesh and used to make the top layer of the substrate. The reservoir is preferably formed by dry blending the GUR 413, GUR 212 and HB301s/HB312 ultra high molecular weight polyethylenes in respective ratios of 15 percent, 41 percent and 44 percent.

Other suitable synthetic resins for the substrate include high density polyethylene, polyvinylidene difluoride, and polyamide. A particular high density polyethylene suitable in the practice of the invention is one distributed by the Hoechst Celanese Corp. as GMVP2250P (typical melt index condition of F of 7). A suitable polyvinylidene fluoride, also known as Kynar, is distributed by Pennwalt Corp. of Philadelphia, Pa. as Pennwalt 301. A suitable polyamide, or Nylon 6, is one sold by Allied Signal Corp. of Morristown, N.J., as Capron 8270 HS.

It will be seen below that particular sizes and shapes of the synthetic resin particles are preferred in the practice of the invention. When the synthetic resin particles are too large, they are suitably ground mechanically or screened to achieve the desired particle size. When a blend of synthetic resins is used, such as the GUR 413, GUR 212 and HB301s/HB312 blend recited above, it will be readily appreciated by those of ordinary skill in the art that the ratio of the components of the blend are adjustable to achieve a desired pore structure in the finished product. For example, an increased percentage of the finest component is employed to produce a product having a smaller pore size. Blending of the resin components is achieved by a wide assortment of commercially available blenders.

The smaller particles forming the top layer 36 will provide a pore size substantially smaller than that of the reservoir, but the pores would not be sufficiently small to entrap microspheres on the order of 5 microns in diameter or smaller on surface 38. To achieve the fine pore size desired, in accordance with one embodiment, a microporous matrix is formed in the pores between the sintered particles of the top layer 36 by casting.

The microporous matrix is formed from a solution impregnated into the pores between the sintered particles of the layer 36 in a manner similar to the way that a microporous membrane is cast from a microporous membrane forming solution. The material of the microporous matrix should be hydrophilic or capable of being rendered hydrophilic. Thus, the microporous matrix is any biochemically inert material, or material that is rendered biochemically inert, which can be cast from a solution within the pores at the top surface of the substrate and which is or can be rendered hydrophilic. The material of the microporous matrix, for example, may be cellulose, polyvinylchloride, polyvinylidene difluoride, polycarbonate, nylon, or polysulfone. Cellulose is preferred, primarily because the process for converting it to a microporous matrix is simpler than the processes for the other listed polymers. The conversion processes for some of these polymers are described in U.S. patent application Ser. No. 837,182, filed March 7, 1986, which is incorporated by reference. Cellulose is also preferred because it is compatible with a large number of immunoassays. A preferred cellulose for use in the practice of the invention is a nitrocellulose wet with isopropyl alcohol manufactured by Hercules, Incorporated, Wilmington, Del. and sold as KS 70-80. This nitrocellulose has a specific gravity of 1.36 and a viscosity rating of 70 to 80 per ASTM 1343-56.

Figure 3:
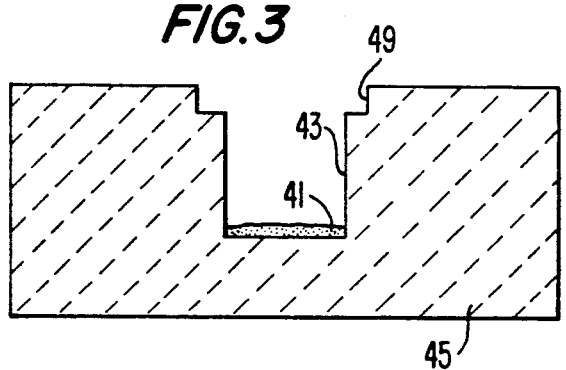
FIGS. 3 and 4 are a sectional view of a mold illustrating successive steps in a method of manufacturing a porous substrate to be used in the apparatus of the present invention.
Figure 4:
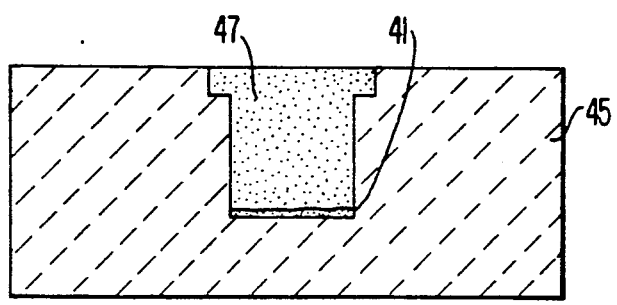

An example of a method of manufacturing the substrate of the invention is illustrated in FIGS. 3 and 4. A layer 41 of GUR 400 Series ultra high molecular weight polyethylene, screened minus 150 mesh, is positioned in the bottom of a cylindrical cavity 43 of mold 45. The particles of the powder are of a size such that 60% or more of the particles will pass through a 150 mesh screen. Prior to positioning the layer of the fine powder 41 in the bottom of the mold cavity, a powdered surfactant in an amount of 0.3% by weight is blended into the powder. Suitable surfactants are those in the form of very fine particle powders of less than 200 mesh, which are capable of blending with and coating the other particles of the blend. A particular surfactant suitable in the practice of the invention is sodium-N-methyl-N-oleoyl taurate, sold as WW5 by Diapolymer Corp., Clifton, N.J. The amount of fine powder forming the layer 41 is not critical, but it needs to be sufficient to completely cover the bottom of the mold cavity. After placing the fine powder in the bottom of the mold cavity, the mold cavity is vibrated to spread the powder evenly over the bottom surface and to insure that it completely covers the bottom surface of the mold cavity.

The remainder of the cavity is then filled with thermoplastic synthetic resin powder 47 having particles that are larger, 100 mesh powder, and preferably are highly irregular in shape. The powder 47 may be the same resin as the layer 41, or it may be another resin which will sinter with the resin of layer 41. The use of irregularly shaped particles in the powder 47 keeps the particles from nesting close together and will result ultimately in a high void volume in the resulting porous structure, for example, 50% or greater. The powder 47 also has a powdered surfactant, 0.3% by weight, blended into it prior to the powder being placed in the mold. The surfactant may be the same as that blended into the fine powder. The larger particle powder 47 fills the cavity 43 of the mold, including a top section 49 of the cavity with an enlarged diameter. The mold is again vibrated to ensure that relatively uniformly sized interstices are formed between the particles of powder 47.

The mold is then heated to sinter the particles together. The heat cycle for sintering the particles suitably involves heating the mold evenly up to 370 degrees Fahrenheit over a ten-minute span, maintaining the mold at 360 degrees Fahrenheit for an additional two minutes, and then cooling the mold down to room temperature over a ten minute span. Those ordinarily skilled in the art will appreciate that this thermal cycle can be varied to accommodate changes in materials, molds, and so forth, and that, further, the mold may be heated by a variety of methods, including hot air ovens, heated and cooled platens, and the like.

Figure 5:
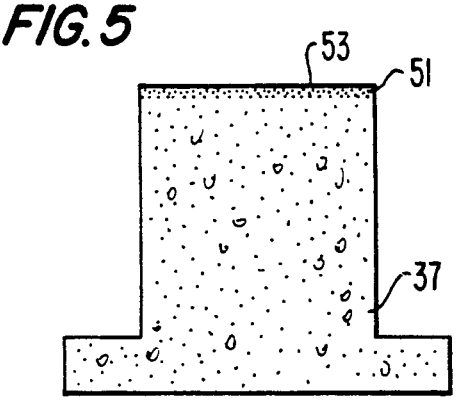
FIG. 5 illustrates a porous slug which is made by the methods illustrated in FIGS. 3 and 4.

After the sintering, the mold is cooled and the slug comprising the sintered particles is removed from the mold. The sintered slug as shown in FIG. 5 at this point will have a top layer 51 that is formed of the fine sintered particles, and that will have a smooth top surface 53 formed by the bottom of the mold with an average pore size in the top layer and at the surface of between 5 and 10 microns. The average pore size formed of the larger particles, which will ultimately comprise the reservoir 37 of the substrate, will range from 20 to 30 microns.

The sintered slug in the form immediately after molding is suitable for entrapping large microspheres in accordance with the invention. The average pore size in the top layer 53 will be between 5 and 10 microns and will entrap microspheres about twice the average pore size or larger at the surface and about ½ the average pore size in the top layer. However, as explained above, it is preferable to use microspheres 5 microns in diameter or less and to trap these microspheres at the surface of the substrate. After sintering the slug together as described above, a microporous matrix is cast within the pores of the substrate adjacent the top surface, while leaving the pores of the reservoir empty. Generally, the casting step is carried out by preparing a solution from which the microporous matrix is formed and impregnating the pores adjacent to the smooth top surface of the slug with the solution. A phase inversion is caused to occur in the impregnated solution and the solid material which becomes the microporous matrix comes out of solution within the pores of the slug adjacent to the top surface of the slug. In this manner, a smooth microporous surface which will entrap the small microspheres is provided.

Examples of solutions for forming the microporous matrix and methods of casting the microporous matrix in the pores are described below:

400 grams of n-butyl alcohol (butanol) is poured into a one-gallon mixing bucket of a commercial mixer capable of running at 2500 rpm. The alcohol is manufactured by Badische Corporation of Freeport, Tex. and has a specific gravity of 0.8109. With the mixer running at a low speed of 1000 rpm, 16 grams of cellulose acetate are slowly added to the butanol. The cellulose acetate is in the form of a white powder having a specific gravity of 1.31 to 1.32, available from Eastman Chemical Products, Inc., Kingsport, Tenn. After the cellulose acetate has been added, the mixer is run at 2500 rpm for one minute at the end of which the cellulose acetate should be dissolved.

132.8 grams of nitrocellulose, which is wet with 30% by weight isopropyl alcohol and which has a viscosity rating between 70 and 80 seconds (ASTM D 1343-56) is added to the mixing bucket and the mixer is run at 2500 rpm for two minutes to dissolve the nitrocellulose.

1079 grams of acetone is poured into the mixing bucket and the mixer is operated at high speed for fifteen minutes. The acetone is of ACS grade and has a molecular weight of 58.08, available from Union Carbide, Danbury, Conn. The selection of the solvents, that is, the n-butyl alcohol and acetone, are critical, since the relative solubility of the nitrocellulose and cellulose acetate materials in these solvents, and the relative evaporation rates of the solvents, are crucial to the phase inversion process that forms the microporous structure. At the end of this mixing step, all of the solids are dissolved in the mixture.

732 grams of butanol is then poured into the mixer and the mixer operated at high speed for two minutes. Then, with the mixer running at 1000 rpm, 100 grams of filtered pure water is dribbled slowly into the solution.

With the mixing speed still running at 1000 rpm, 24 grams of colorant-grade titanium dioxide ($TiO_2$) are mixed into the solution, after which the mixer is run at 3200 rpm for fifteen minutes so that the titanium dioxide is thoroughly mixed and in suspension in the liquid of the solution. The titanium dioxide is an extremely fine powder of less than 325 mesh and is used to improve the "whiteness" of the microporous layer. Other chemically inert colorants available in a fine powder form are suitable in the practice of the invention.

The mixture is then poured into a closed container which has a small space above the top of the solution. The mixture will contain air bubbles as a result of the mixing process. The solution is allowed to stand for several hours, during which time the bubbles in the solution will rise to the surface and escape. During the removal of the bubbles, the temperature of solution is kept above 80 degrees F. The finished mixture, after removal of the air bubbles, at 90 degrees F., should have a viscosity of 400 to 800 centipoise (cps) and is ready to be impregnated into the fine pores adjacent to the smooth top surface of the porous plastic slug. In the casting process for this example, a phase inversion is caused to occur by the evaporation of the solvents, leaving behind the microporous matrix as a residue within the pores of the substrate. In order to achieve consistent repeatable results in the porosity of the microporous matrix, the casting process should be performed in a controlled environment. Preferably the relative humidity should be kept between 70 and 80 percent and the ambient temperature should be kept between 78 and 82 degrees F.

In the casting process, the solution is heated to a temperature of between 110 and 115 degrees F., which will drop the viscosity of the solution to below 500 centipoise. A plurality of the slugs formed as described above are oriented in a rack so that the smooth top surface of the slug protrudes below the bottom of the rack. The heated casting solution is poured into a shallow trough and the rack is placed over the trough so that the smooth surface of the slugs are immersed approximately ⅛ of an inch deep into the solution at which time the mixture in the trough will impregnate the pores at the top surface. The tops of the slugs are allowed to remain in the solution for approximately 1 second, whereupon the rack is lifted straight up and then turned over slowly enough for the excess fluid to run off. The rack with the smooth top surfaces facing upwardly with the solution now impregnated in the fine pores adjacent to the top surface is placed under an exhaust hood containing an exhaust fan which is operated to draw air over the impregnated slugs. With a hood having a lower inlet end of 26 inches by 38 inches, the air is exhausted from the hood at a rate of 75 cubic feet per minute to achieve a desired rate of air flow over the impregnated slugs. These steps are all performed while maintaining the controlled humidity and temperature as described above. The impregnated slugs are allowed to sit under the exhaust hood while air is being drawn over the slugs for sufficient time for the solvents to evaporate and the microporous matrix to form and harden in the slug. This time interval will be at least 1½ hours. The parts are then removed from the controlled environment and approximately 0.5 milliliters of a dilute surfactant solution is applied to the smooth top surface of each substrate. For example, the solution may be 1% by weight of betaine, 10% by weight isopropyl alcohol, and 89% by weight filtered water. Betaine is available in liquid form as Varion CADG-LS from Sherex Corp. of Dublin, Ohio. Another suitable surfactant is polysorbate 20 NF, available in liquid form from ICI Americas, Inc., Wilmington, Del. Other suitable surfactants are those that are soluble in a liquid that will wick into the porous plastic and that have a chemical structure that does not interfere with the chemistry of the immunoassay to be performed on the substrate. After application of the surfactant solution, the parts are then placed in a moving air stream to dry them, whereupon the manufacture of the substrates is completed.

The above example will result in a substrate which is microporous at the top surface 38 and macroporous in the reservoir 37 with a high void volume of over 50%, the reservoir pores being in capillary communication with the micropores at the smooth top surface of the substrate. The substrates prepared in accordance with this example will consistently trap on their top surfaces polystyrene microspheres as small as 1.0 micron in diameter.

Figure 9:
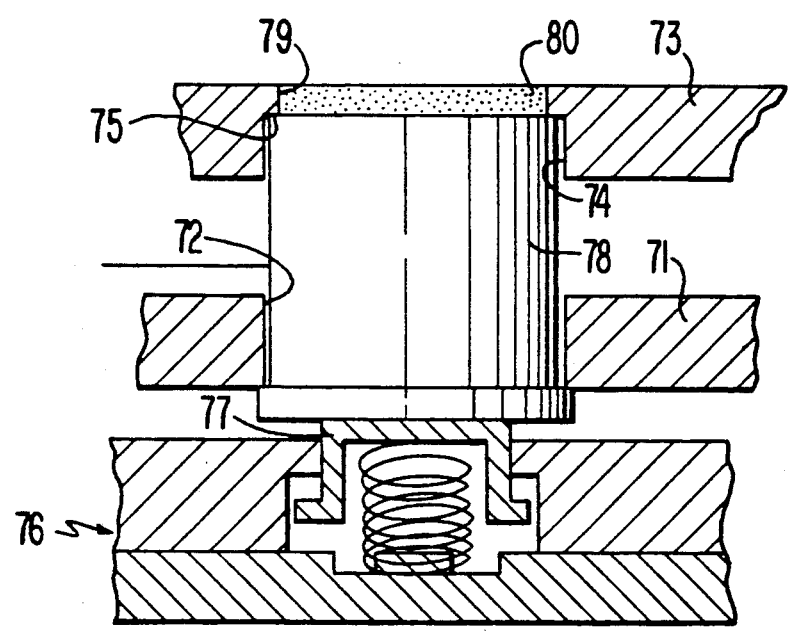
FIG. 9 is a sectional view of a portion of a casting apparatus showing a way of applying a casting solution to a macroporous slug in order to cast a microporous matrix in the top surface of the macroporous slug to produce the porous substrate of the present invention.

Another way of casting the microporous matrix in the top surface of the macroporous slug is illustrated in FIG. 9. In this method, a midplate 71 is employed having a plurality of apertures 72, each of which corresponds in size to the size of the top surfaces in which the microporous matrix is to be cast. The midplate 71 is placed over a casting plate 73 having apertures 74 in alignment with the apertures 72. The apertures 72 and 74 are round to conform with the round shape of the macroporous slugs. The apertures 74 are stepped to have a slightly smaller diameter on their upper side than their lower side, e.g., 0.4 inches in diameter smaller to leave a 0.2 inch shoulder 75 within each aperture 74. The upper end of the aperture 74 is sized to be slightly smaller than the size of the slug, so that when a slug is inserted into the lower end of the aperture 74, the top surface of the slug 78 will be stopped by the shoulder 75.

When the midplate 71 is placed over the casting plate 73, the casting plate 73 will be inverted or upside down from the position shown in FIG. 9 so that the larger end of the opening 74 faces upwardly. The casting plate 73 is provided with dowel pins (not shown) to align the midplate 71 with the plate 73, whereby apertures 72 are aligned with the apertures 74. With the assembled plates sitting upside down on a table and with the plate 71 positioned over the plate 73, the porous slugs 78 to receive the microporous matrix are inserted into the aligned apertures 72 and 74 with the top surfaces of the slugs facing down. After the slugs have been inserted into the aligned apertures, a spring plate assembly 76 is placed upside down on the top of the plates 71 and 73. The spring plate 76 has spring-loaded buttons 77 which align with the apertures 72 and 74 and when the spring plate 76 has been placed upside down over the assembled plate 71 and 73 with the porous slug 78 inserted into the aligned apertures, the buttons 77 push against the bottoms of the porous slugs. The upside down assembly of the casting plate 73, the midplate 71 and the spring plate assembly 76 is turned right side up and placed on a flat surface in the casting room so that the entire assembly of the plates 71, 73, and 76 is as shown in FIG. 9.

With the casting room set to the proper environment, e.g., 85 degrees Fahrenheit and 70 percent relative humidity, the casting solution is heated to the proper temperature, e.g., 115-120 degrees Fahrenheit, and the casting solution is dispensed onto the top of the casting plate so that the casting solution fills the wells 79 formed by the smaller upper portions of the apertures 74 over the slugs 78. A typical way of dispensing the solution would be to use a dispensing box which would have a plurality of valves which can be opened simultaneously with each valve aligned with a row of slugs inserted into the assembled plates 71 and 73, thus dispensing the casting solution into all of the wells 79 in a rapid manner. The volume of the casting solution dispensed should be in excess of the volume required to fill the wells 79 so that each well 79 is filled to overflowing. After the casting solution has been dispensed, a blade is drawn over the top of the casting plate to remove the excess casting solution resulting in a layer of solution 80 filling each well 79. The shoulders 75 are positioned so that the wells 79 preferably have a depth of 0.030 inches. The depth of the wells should be deep enough to insure that the entire exposed top surface of the slug is impregnated with the casting solution and is shallow enough that no skin forms on the solution before it disappears from above the top surface of the slug by wicking into the slug or by evaporation.

Immediately after the blade has been drawn over the casting plate (within about 30 seconds), the casting plate is removed from the assembly while the impregnated slugs are held in place by the midplate. The casting plate must be removed very soon after the excess solution has been removed from the top of the casting plate to prevent solids which are precipitating out of the solution from adhering to the casting plate. If solids were allowed to adhere to the casting plate, this would result in surface defects in the finished parts. After all the casting solution has wicked into or evaporated off of the porous slugs, the midplate 71 may be slid off of the spring plate assembly 76 with the impregnated slugs retained in the apertures 72 of the midplate by friction. The midplate is then separated from the impregnated slugs, which are then left to harden in the controlled environment as described above.

To make the microporous top surface of the finished porous substrate hydrophilic after the parts have been hardened, they are removed from the casting room and approximately 0.4 milliliters of a surfactant solution, as described above, is pipetted onto the center of the top surface of each slug.

By changing the parameters of the solution from which the microporous matrix is cast, the porosity of the microporous matrix can be varied so as to entrap other sizes of microspheres. If the percentages of the solids added to the solution is increased, the pore size of the microporous matrix will be reduced. If the molecular weight of the nitrocellulose is increased, the pore size will be reduced. The molecular weight of nitrocellulose is usually specified by the vendor as a viscosity rating per ASTM D 1343-56.

Listed below are some specific examples of formulas for the casting solution which will produce different pore sizes ranging from 0.3 micrometers to 1.2 micrometers in the microporous matrix:

Formula to achieve microporous matrix pore size of 0.3 um

Butanol—3,723.5 gr
Acetone—3,548.1 gr
NC—773.6 gr
CA—93.2 gr
H₂O—329.1 gr

Formula to achieve microporous matrix pore size of 0.8 um

Butanol—3,766.4 gr
Acetone—3,590.0 gr
NC—736.4 gr
CA—88.7 gr
H₂O—332.7 gr

Formula to achieve microporous matrix pore size of 1.0 um

Butanol—3,885.9 gr
Acetone—3,704.0 gr
NC—605.5 gr
CA—72.9 gr
H₂O—343.3 gr

Formula to achieve microporous matrix pore size of 1.2 um

Butanol—962.2 gr
Acetone—917.2 gr
NC—137.8 gr
CA—16.0 gr
H₂O—85.0 gr

In order to get the cellulose acetate to go more easily into solution, it can be predissolved in a portion of the acetone in the above formulas. This initial cellulose acetone solution may, for example, be 6.4 percent by weight cellulose acetate and 93.6 percent by weight acetone. When this initial mixture of the cellulose acetate and the acetone is made, the mixture is shaken to homogenize the mixture and then the amount of the resulting solution which will provide the desired concentration of cellulose acetate in the ultimate casting solution is weighed out. The acetone which was added to the initial mixture of cellulose acetate and acetone is then subtracted from the amount of acetone to be employed in the casting solution to determine the amount of straight acetone to be subsequently added to the solution, so that the total amount of acetone in the formula remains the same. In another specific example, the initial amounts of the liquids used in the solution, butanol, acetone, and water are reduced by 40% from the first described specific example and 132.8 grams of nitrocellulose with a viscosity rating between 140 and 180 seconds is substituted for nitrocellulose of the above-described example. The resulting solution will have a viscosity of 3500-5500 cps. The solution is heated to a temperature of between 125 and 135 degrees F., which will drop the viscosity below 3000 cps., and the solution is impregnated into the top surface of the slugs by dipping as described above. With these changes, and otherwise following the first specific example as described above, the pore size of the resulting microporous matrix is reduced so that the top surface will trap microspheres down to 0.3 microns in size.

Instead of dipping the slugs into the microporous matrix forming solution, the solution may be dispensed onto the smooth top surface of the slugs by means of a dispensing gun. As in the dipping process, the entire operation of applying the solution to the top surfaces of the slugs should be performed in a controlled environment. The relative humidity of the environment should be kept between 70 and 80 percent and the temperature should be kept between 78 and 82 degrees Fahrenheit. The membrane solution of the first described example is heated to a temperature of 110 to 115 degrees Fahrenheit to drop the viscosity of the solution below 500 cps. The heated solution is put into a heated fluid dispensing gun and by means of the gun, a measured amount of the solution is dispensed from the gun onto each slug top surface. The amount of the solution dispensed is selected to be a little more than enough to cover the top surface. The microporous matrix is then allowed to form from the solution within the pores of the top surface under an exhaust hood as described before. After hardening of the microporous matrix, the dilute surfactant solution is applied as described before. The resulting structures will consistently trap on their top surfaces 1.0 micron polystyrene microspheres.

Another way of achieving a microporous matrix which will entrap 0.3 micron microspheres is to dispense a second measured amount of the solution into the top surface of each slug from the gun. The second measured amount is preferably dispensed onto the top surface at least a few minutes after dispensing the first measured amount so that the microporous matrix from the first measured amount has begun to form. The parts are then dried again for 1.5 hours under the drying hood in the same manner as described above. This repeated application of the microporous matrix forming solution will decrease the pore size in the matrix in a top surface so that the top surface will entrap 0.3 micron microspheres.

The above-described examples will entrap microspheres of the size described with no proteins bonded to the surface of the microspheres and will entrap microspheres with antibodies on the microspheres of the same size if there is no chemical attraction between the antibodies and the material of the microporous matrix. However, if there is a chemical attraction between the antibodies on the surface of the microsphere and the material of the microporous matrix, then the structure will entrap still smaller microspheres. For example, in the example which will entrap one micron microsphere, if there is a chemical attraction between the antibodies and the cellulose material of the microporous matrix, then microspheres down to 0.5 microns can be entrapped at the top surface of the structure.

In an alternative embodiment, the substrate is made without the use of a microporous matrix cast within the pores of the top layer. In this embodiment, the top layer is instead formed of a very fine thermoplastic synthetic resin powder, e.g., GUR 400 Series ultra high molecular weight polyethylene powder, modified by vibrating it over a 200 mesh (U.S. sieve) screen so that at least 90% of the particles are small enough to pass through the screen. A powder in which the particles will pass through a 200 mesh screen is referred to as being "minus 200 mesh". Thus, the powder employed is 90% minus 200 mesh.

Figure 6:
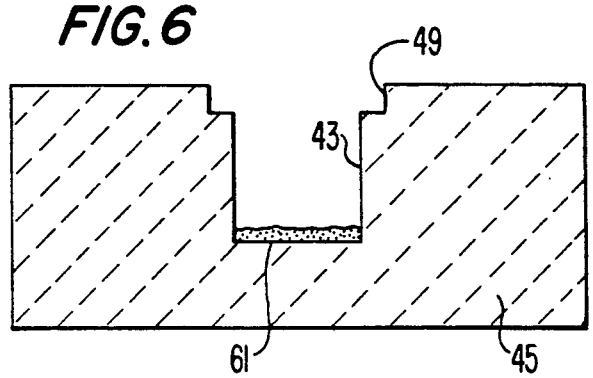
FIGS. 6 through 8 illustrate sectional views through a mold illustrating the steps of an alternative method of making a porous substrate to be employed in the apparatus of the present invention.
Figure 7:
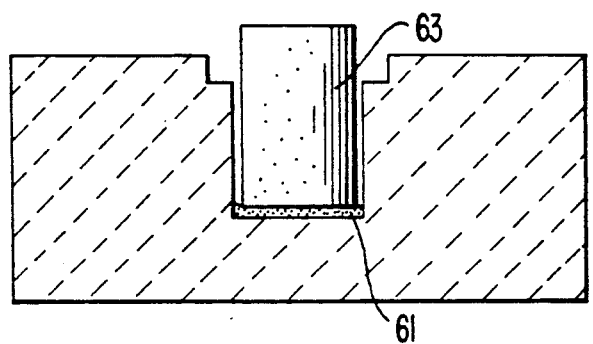
Figure 8:
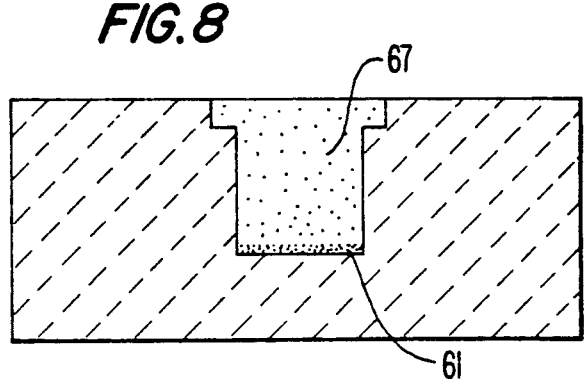

The fine powder produced as described above is blended with 0.3% by weight of surfactant, which may, for example, be sodium-N-methyl-N-oleoyl taurate. The mixture of the powder and the surfactant is dispensed into the cavity 43 of the mold 45 as shown in FIG. 6. The mold is vibrated to spread the fine powder evenly over the bottom of the cavity 43 into a layer 61. The amount of powder dispensed in the cavity is not critical but it should be sufficient to completely cover the bottom of the mold cavity. After the powder has been spread evenly over the bottom of the mold, a cylindrical pin 63 having a diameter slightly smaller than the diameter of the lower part of the cavity 43 is inserted into the cavity and pressed against the layer 61 of fine powder with a force of 5000 to 15000 pounds per square inch to compress the powder as shown in FIG. 7. This compression reduces the size of the interstices between the particles of the fine powder and, accordingly, will reduce the pore size in the top layer 36 of the substrate being produced. The greater the compressive force applied to the layer 61, the smaller will be the pore size in the top layer 36 of the resulting substrate. A force of 11,000 pounds per square inch will produce an average pore size diameter in the top layer 36 of the resultant substrate of about 3 microns. After the layer 61 has been compressed, the remainder of the mold cavity 63 is filled with larger particle synthetic resin powder 67, e.g., 150 mesh ultra high polyethylene powder, as shown in FIG. 8. Powder 67 is the blend of GUR 413, GUR 212, and HB301s/HB312 recited above. The powder 67 will also have a surfactant, 0.3% by weight, blended therein. The surfactant may be the same as in the fine powder of the layer 61. The mold is then again vibrated for about 20 seconds to achieve a more uniform spacing between the particles 67. This vibration will not substantially affect the compressed layer 67. The mold is then heated to sinter the particles of the layer 61 and the particles of the powder 67 together and the two layers together at their interface. The mold is then cooled and the finished substrate is dropped out of the mold. The resulting substrate will have a top layer 35 which is microporous and a reservoir 37 which is macroporous and which is in capillary communication with the microporous layer. The microporous top layer will entrap microspheres of about 5 microns on the top surface if there is no chemical bonding between antibodies in the microspheres and the material of the top layer 35. If chemical bonding occurs, the top surface and layer will entrap smaller microspheres. The top layer will also trap microspheres down to a micron in diameter distributed through the top layer.

In the immunoassay apparatus described above, a one piece porous substrate performs the function of entrapping microspheres at the surface of the substrate or in the top layer while at the same time acting as a reservoir to accumulate the liquids that are passed through the upper surface of the substrate in the immunoassay process. Thus, the problems of assembly of components of the substrate and problems of gaps between components of the substrate are completely avoided.

The above description is of preferred embodiments of the invention and modification may be made thereto without departing from the spirit and scope of the invention, which is defined in the appended claims.

What is claimed is:

1. A diagnostic apparatus comprising a one piece open celled porous substrate defining a top surface and a lower reservoir section and a top layer, said top layer being microporous and biochemically inert, said reservoir portion being macroporous and being in capillary communication with the micropores of said top surface, wherein said micropores are of a size sufficient to trap, in or on the top layer, microspheres of a diameter of 5 microns or less, the pores in said reservoir portion having an average size of at least 20 microns in diameter, said reservoir portion having a substantially greater volume than said top layer.

2. A diagnostic apparatus as recited in claim 1, wherein said substrate is contained within a container, said container having a top opening exposing said top surface and having a closed bottom opposite said top opening.

3. A diagnostic apparatus as recited in claim 1, wherein microspheres are located in or on said top surface.

4. A diagnostic apparatus as recited in claim 1, wherein said substrate comprises sintered particles of synthetic resin and a microporous matrix cast into the pores of said substrate at said top surface.

5. A diagnostic apparatus as recited in claim 4, wherein said top layer comprises particles which are smaller than the particles which comprise said reservoir portion.

6. A diagnostic apparatus as recited in claim 4, wherein said microporous matrix is formed from a casting solution comprising from about 44.0 to 45.4 parts by weight of butanol, from about 41.9 to 43.3 parts by weight of acetone, from about 6.5 to 9.1 parts by weight of nitrocellulose, from about 0.8 to 1.1 parts by weight of cellulose acetate, and from about 3.9 to 4.0 parts by weight of water.

7. A diagnostic apparatus comprising a one piece open celled pore substrate having a microporous biochemically inert top layer and a macroporous reservoir portion below said top layer, said top layer having micropores of the size to entrap microspheres of a diameter of 5 um or less on or in said top layer when applied to said top layer in a liquid suspension, the pores in said reservoir portion having an average pore size of at least 20 microns in diameter and being in capillary communication with the micropores of said top layer, said reservoir portion having a substantially greater volume than said top layer.

8. A diagnostic apparatus as recited in claim 7, further comprising a container containing said substrate and defining an opening exposing the surface of said top layer and having a closed bottom opposite said opening.

9. A diagnostic apparatus as recited in claim 7, wherein microspheres are entrapped in or on said top layer.

10. A diagnostic apparatus as recited in claim 7, wherein said substrate comprises sintered particles of synthetic resin in said top layer and said reservoir portion and wherein said top layer comprises particles which are smaller than the particles in said reservoir portion.

11. A diagnostic apparatus as recited in claim 10, wherein a microporous matrix is cast into the pores of said top layer adjacent to the top surface thereof.

12. A diagnostic apparatus as recited in claim 11, wherein said microporous matrix is formed from a casting solution comprising from about 44.0 to 45.4 parts by weight of butanol, from about 41.9 to 43.3 parts by weight of acetone, from about 6.5 to 9.1 parts by weight of nitrocellulose, from about 0.8 to 1.1 parts by weight of cellulose acetate, and from about 3.9 to 4.0 parts by weight of water.

13. A diagnostic apparatus as recited in claim 10, wherein said top layer of sintered particles is formed by distributing said smaller particles in a layer and applying a compressive force to said layer to reduce the size of the interstices between said smaller particles and then sintering said smaller particles together.

14. A diagnostic apparatus as recited in claim 7, wherein said substrate comprises particles of synthetic resin and a microporous matrix cast within the pores of said top layer adjacent to the top surface of said layer.

15. A diagnostic apparatus comprising a one piece open celled porous substrate defining a top layer and said top surface and a lower reservoir section and a top layer, said top surface being microporous, said reservoir portion being macroporous and being in capillary communication with the micropores of said top layer, and microspheres located in or on said top layer wherein said micropores are of a size sufficient to trap, in or on the top layer, microspheres of a diameter of 5 microns or less, the pores in said reservoir portion having an average size of at least 20 microns in diameter, said reservoir portion having a substantially greater volume than said top layer.

* * * * *